United States Patent [19]

Wang et al.

[11] 4,321,274

[45] Mar. 23, 1982

[54] **SUBSTITUTED 1-(CINNAMYLIDENEAMINO)-3-BENZYLI-DENEAMINOGUANIDINES ACTIVE AGAINST *GIARDIA LAMBLIA* AND *TRICHOMONAS VAGINALIS***

[75] Inventors: Ching C. Wang, Watchung; Michael H. Fisher, Ringoes, both of N.J.

[73] Assignee: Merck & Co., Inc., Rahway, N.J.

[21] Appl. No.: 194,714

[22] Filed: Oct. 6, 1980

[51] Int. Cl.³ .................. A61K 31/16; A61K 31/155; A61K 31/255; A61K 31/275
[52] U.S. Cl. .................................. 424/304; 424/303; 424/309; 424/316; 424/320; 424/321; 424/324; 424/326
[58] Field of Search ............... 424/304, 326, 309, 303, 424/324, 316, 320, 321

[56] References Cited

U.S. PATENT DOCUMENTS 3,816,530  6/1974  Linn ................................ 260/564 F
3,856,975 12/1974  Linn ................................ 424/304

OTHER PUBLICATIONS

Altman, L. K., The New York Times, Jun. 10, 1980, p. C-1.
Dykers, Medical Intelligence, vol. 293, pp. 23–24, (1975).
Kerlin et al., Digestive Diseases, vol. 23, pp. 940–942, (1978).
Hartong et al., Gastro enterology, vol. 77, pp. 61–69, (1979).
Craun. The American Journal of Public Health, vol. 69, pp. 817–819, (1979).
Fouts et al., The Journal of Infectious Diseases, vol. 141, pp. 137–143, (1980).
Wisdom et al., The British Journal of Venereal Diseases, vol. 41, pp. 90–96, (1965).
Naguib et al., The Journal of Obstetrics and Gynecology, vol. 27, pp. 607–616, (1966).
Hughes et al., Journal of Obstetrics and Gynecology of the British Commonwealth, vol. 73, pp. 821–827, (1966).
Ings et al., Biochemical Pharmacology, vol. 23, pp. 1421–1429, (1974).
Collection of Monographs from International Conference on the Chemistry, Pharmacology, and Clinical Application of Nitroimidazoles, Aug. 1980, pp. 33–36, 53–54, 61–62 and 67.

*Primary Examiner*—Allen J. Robinson
*Attorney, Agent, or Firm*—David L. Rose; Harry E. Westlake

[57] ABSTRACT

Substituted-1-(cinnamylideneamino)-3-benzylideneaminoguanidines, known as effective anti-coccidial agents, are useful as potent anti-giardiasis and anti-trichomoniasis agents.

2 Claims, No Drawings

SUBSTITUTED 1-(CINNAMYLIDENEAMINO)-3-BENZYLI-DENEAMINOGUANIDINES ACTIVE AGAINST *GIARDIA LAMBLIA* AND *TRICHOMONAS VAGINALIS*

BACKGROUND OF THE INVENTION

*Giardia lamblia*, a parasite that until recently was widely believed to be relatively harmless, now heads the list of the most common intestinal parasitic infections in the United States and some other countries. The parasite causes a diarrheal disease called giardiasis.

This infection causes a variety of intestinal symptoms, such as prolonged diarrhea, abdominal cramps, stomach pain, severe weight loss, fatigue, nausea and flatulence.

Giardiasis can also cause malabsorption of nutrients and even retarded growth. Furthermore, giardiasis can mimic the symptoms of other conditions such as ulcers and gall bladder attacks. If misdiagnosed, a patient may have a series of costly, needless tests, and even surgery.

The infection can be successfully treated with one of three drugs: Atabrine, Flagyl or furazolidone. However, each of these drugs is known to cause adverse side effects. Until the present invention no prophylactic drug has been found which can adequately protect against giardiasis. (L. K. Altman, M.D., The New York Times, June 10, 1980).

Trichomoniasis is an infection of the lower genitourinary tract, which may be induced in men and women by the protozoan parasite *Trichomonas vaginalis*. The infection may produce a few symptoms of such extreme discomfort and morbidity that intervention from a gynecologist or a urologist is necessary. The disease is of cosmopolitan distribution and apparently 10–25% of sexually mature females and 25–80% of their consorts are involved (E. A. Steck, The Chemotherapy of Protozoan Diseases, Vol. II, Section 3, 17-1 (1971). Trichomoniasis is presently treated with Flagyl(metronidazole).

The present invention relates to the use of a group of substituted 1-(cinnamylideneamino)-3-benzylideneamino-guanidines which are more active and less toxic than Flagyl (metronidazole) and other commonly used drugs in the treatment of giardiasis and trichomoniasis in humans.

The substituted 1-(cinnamylideneamino)-3-benzylideneaminoguanidines and methods of preparation thereof have been disclosed in U.S. Pat. Nos. 3,816,530 and 3,856,975 and are herein incorporated by reference.

The utility disclosed in these patents is essentially the control of coccidiosis particularly the control of poultry coccidiosis. The causative organisms of coccidiosis are of the genus Eimeria.

SUMMARY OF THE INVENTION

The present invention is directed to the novel method for control and treatment of giardiasis, a parasitic infection in humans caused by protozoa of the genus Giardia. As reported in the New York Times article, cited above, there is no drug which can adequately protect against giardiasis.

The novel compositions used in the present method can also be used for the prevention, treatment and control of trichomoniacis in men and women. Successful therapy of trichomoniasis with Flagyl(metronidazole) has been reported, however, the drug is mutagenic in bacteria and has been shown to be carcinogenic in animals.

Therefore, it is an object of the present invention to (1) provide for novel pharmaceutical compositions comprising a 1-(cinnamylideneamino)-3-benzylideneaminoguanidine derivative with anti-giardiasis and anti-trichomoniasis activities; (2) provide a novel method for the prevention, control and/or treatment of giardiasis and trichomoniasis in humans through the administration of the novel compositions.

DETAILED DESCRIPTION OF THE INVENTION

The 1-(cinnamylideneamino)-3-benzylideneaminoguanidines to be used in the method of present invention have the structural formula:

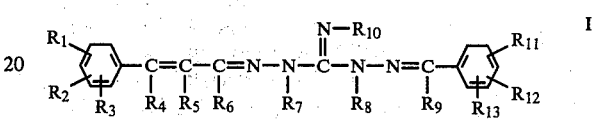

and acid addition salts thereof, where $R_1$ and $R_{11}$, are each hydrogen, halo, nitro, trifluoromethyl, trifluoromethoxy, trifluoromethylthio, acetyl, carbamoyl, cyano, methylsulfinyl, methylsulfonyl, carbomethoxy or dimethylaminosulfonyl; $R_2$ and $R_{12}$ are each hydrogen, halogen or nitro; $R_3$ and $R_{13}$ are each hydrogen or halogen. At least one of $R_1$, $R_2$, $R_3$, $R_{11}$, $R_{12}$ and $R_{13}$ is a substituent other than hydrogen. In the above formula $R_4$ and $R_5$ are each hydrogen, halogen or lower alkyl; $R_6$, $R_7$ $R_8$ and $R_9$, are each hydrogen or lower alkyl; and $R_{10}$ is hydrogen, lower alkyl or lower alkanoyl. In the above definitions halogen includes chloro, bromo, fluoro or iodo, lower alkyl includes alkyl of 1–5 carbons such as methyl, ethyl, isopropyl or pentyl, and lower alkanoyl also includes 1–5 carbons such as acetyl, propionyl, butyryl and the like.

These compounds and the method of preparation thereof are disclosed in U.S. Pat. Nos. 3,816,530 and 3,856,975.

The preferred substituted 1-(cinnamylideneamino)-3-benzylideneaminoguanidines are selected from the following compounds:

(1) 1-(4-chlorocinnamylideneamino)-3-(3,4-dichlorobenzylideneamino)guanidine;
(2) 1-(4-trifluoromethylcinnamylideneamino)-3-(4-chlorobenzylideneamino)-3-methylguanidine;
(3) 1-(4-cyanocinnamylideneamino)-3-(4-chlorobenzylideneamino)-3-methyl-guanidine;
(4) 1-(3,4-dichlorocinnamylideneamino)-3-(4-chlorobenzylideneamino)-3-methyl-guanidine;
(5) 1-(4-cyanocinnamylideneamino)-3-(4-trifluoromethylbenzylideneamino)-3-methyl-guanidine;
(6) 1-(3,4-dichlorocinnamylideneamino)-3-(4-trifluoromethylbenzylideneamino)-3-methyl-guanidine;
(7) 1-(3,4-dichlorocinnamylideneamino)-3-(4-cyanobenzylideneamino)guanidine;
(8) 1-(4-chlorocinnamylideneamino)-3-(4-chlorobenzylideneamino)-3-methyl-guanidine;
(9) 1-(4-chlorocinnamylideneamino)-3-(4-trifluoromethylbenzylideneamino)-3-methyl-guanidine; and
(10) 1-(4-trifluoromethylcinnamylideneamino)-3-(4-nitrobenzylideneamino)-3-methyl-guanidine.

The pharmaceutically acceptable salts of the above compounds include hydrohalides such as hydrochloride, hydrobromide; nitrate; fluorosulfate; sulfate or methosulfate; phosphate; or salts resulting from the neutralization of the base with an organic acid such as maleic, fumaric, tartaric, citric, acetic, salicylic, succinic, benzoic, benzenesulfonic, glutamic or lactic acid. Such salts are equally active anti-giardiasis or anti-trichomoniasis agents.

The activity of these compounds against *Giardia lamblia* and *Trichomonas vaginalis* are shown by the following test:

About 1.0–2.0 ml of a nutrient medium, for example, the modified Diamond's TPS medium at pH 7.05, together with about 10% by volume of heat-inactivated serum and about 1% by volume of antibiotic-antimycotic solution is placed in each well of a multiwell plate. To this mixture, an aliquot of a suspension of *G. lamblia* cells containing about $10^6$ organisms is added. Subsequently, each well is inoculated with a known concentration of one of the active compounds, for example, 1-(3,4-dichlorocinnamylideneamino)-3-(4-cyanobenzylideneamino)guanidine. The multiwell plate containing the individual culture samples is incubated under anaerobic conditions at about 37° C. for about 16–24 hrs. The number of viable cells remaining in each well are then counted, such as with a hemacytometer. The percentage of survival is determined by comparison to controls inoculated with DMSO (dimethylsulfoxide) and the effective concentration (in parts per million) for 50% inhibition of growth ($ED_{50}$) is determined. It is established that the lower the number of the value of $ED_{50}$, the higher the activity of the active compound. The $ED_{50}$ values of some of the active compounds are summarized below in Table I.

TABLE 1

In vitro Anti-*G. lamblia* and anti- *T. vaginalis* activities of Substituted 1-(cinnamylideneamino)-3-benzylideneaminoguanidines

| | Compound | Anti-*G. lamblia* $ED_{50}$ (ppm) | Anti-*T. vaginalis* $ED_{50}$ (ppm) |
|---|---|---|---|
| (1) | 1-(4-chlorocinnamylideneamino)-3-(3,4-dichlorobenzylideneamino)guanidine | 1.10 | 2.25 |
| (2) | 1-(4-trifluoromethylcinnamylideneamino)-3-(4-chlorobenzylideneamino)-3-methyl-guanidine | 0.80 | 2.75 |
| (3) | 1-(4-cyanocinnamylideneamino)-3-(4-chlorobenzylideneamino)-3-methyl-guanidine | 0.85 | 3.25 |
| (4) | 1-(3,4-dichlorocinnamylideneamino)-3-(4-chlorobenzylideneamino)-3-methyl-guanidine | 0.58 | 2.50 |
| (5) | 1-(4-cyanocinnamylideneamino)-3-(4-trifluoromethyl benzylideneamino)-3-methyl-guanidine | 1.50 | 3.25 |
| (6) | 1-(3,4-dichlorocinnamylideneamino)-3-(4-trifluoromethylbenzylideneamino)-3-methyl-guanidine | 0.73 | 2.67 |
| (7) | 1-(3,4-dichlorocinnamylideneamino)-3-(4-cyanobenzylideneamino)guanidine | 0.57 | 1.00 |
| (8) | 1-(4-chlorocinnamylideneamino)-3-(4-chlorobenzylideneamino)-3-methyl-guanidine | 1.40 | 2.67 |
| (9) | 1-(4-chlorocinnamylideneamino)-3-methyl-guanidine | 1.30 | 2.38 |
| (10) | 1-(4-trifluromethylcinnamylideneamino)-3-(4-nitrobenzylideneamino)-3-methyl-guanidine | 1.00 | 3.25 |

TABLE 1-continued

In vitro Anti-*G. lamblia* and anti- *T. vaginalis* activities of Substituted 1-(cinnamylideneamino)-3-benzylideneaminoguanidines

| Compound | Anti-*G. lamblia* $ED_{50}$ (ppm) | Anti-*T. vaginalis* $ED_{50}$ (ppm) |
|---|---|---|
| Flagyl (metronidazole) | 6.20 | <1.00 |

The present method comprises the administration of an active compound, for example, 1-(4-trifluoromethylcinnamylideneamino)-3-(4-chlorobenzylideneamino)-3-methyl-guanidine, as an anti-giardiasis or anti-trichomoniasis agent to a human patient in amounts ranging from about 0.05 to about 50 mg. per kg. of body weight, preferably from about 0.25 to about 25 mg. per kg. of body weight in a single dose or in 2 to 4 divided doses.

These compounds in the described dosages are usually administered orally. They may also be administered to individuals by injection. The oral pharmaceutical compositions of this invention usually consist of an active compound and some appropriate excipients and used in the form of tablets, troches, capsules, elixirs, suspensions, syrups, wafers, chewing gum and the like. The amount of an active compound in such a therapeutically useful composition or preparation usually ranges from about 2.5 mg. to about 2.5 g. preferably from about 5 mg. to about 500 mg. per unit dosage.

The previously described tablets, troches, capsules, pills and the like usually contain one or more of the following inactive ingredients: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin and/or a flavoring agent such as peppermint, oil of wintergreen, or cherry flavoring. When the dosage unit form is a capsule, it may contain in addition to materials of the above type, a liquid carrier such as fatty oil. Various other materials may be present as coatings or to otherwise modify the physical form of the dosage unit, for instance, tablets, pills, or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially nontoxic in the amounts employed.

EXAMPLE 1

In each well of a multiwell plate is placed 1.4 ml of media mix containing Diamond's TPS medium (see Table 2) at pH 7.05, 10% by volume of heat-inactivated fetal bovine serum, and 1% by volume of an antibiotic-antimycotic solution (see Table 3). A suspension of *Giardia lamblia* is centrifuged at 2,500 xg. for 6 minutes. The cells are resuspended in a small volume of the Diamond's medium, counted, and each well inoculated with approximately $10^6$ organisms. A stock solution of 1-(4-chlorocinnamylideneamino)-3-(3,4-dichlorobenzylideneamino)guanidine in dimethylsulfoxide is made at a concentration of 150 μg/ml. The wells are then inoculated with various concentrations of the drug. The plates are incubated for 24 hours at 37° C. in an anaerobic Gas Pak jar. After 24 hours of incubation each well is mixed and counted for viable organisms using a hemacytometer. The percentage of survival is determined by comparing the treated wells to controls treated with dimethylsulfoxide. The in vitro anti-*G. lamblia* activity of 1-(4-chlorocinnamylideneamino)-3-(3,4-dichlorobenzylideneamino)guanidine is determined in terms of $ED_{50}$ (effective dosage for 50% inhibition of growth) and has a $ED_{50}$ value of 1.10 ppm.

TABLE 2

| Composition of Diamond's TPS Medium | |
|---|---|
| Ingredients | Amounts |
| Trypticase (BBL) | 1.00 g |
| Panmede, liver digest P & B | 2.00 g |
| Glucose | 0.50 g |
| L-cysteine monohydrochloride | 0.10 g |
| Ascorbic acid | 0.02 g |
| Sodium chloride | 0.50 g |
| Potassium phosphate-monobasic | 0.06 g |
| Potassium phosphate, dibasic anhydrous | 0.10 g |
| Water, glass distilled | 87.50 ml |
| pH adjusted to 7.0 with 1 N NaOH | |

TABLE 3

| Composition of antibiotic-antimycotic solution (100X) | |
|---|---|
| Penicillin, | 10,000 units |
| Streptomycin | 10,000 mcg. |
| Fungizone® | 25 mcg. |
| Prepared in 1 ml. of normal saline. | |

Employing substantially the similar procedure as described in Example 1 but substituting for 1-(4-chlorocinnamylideneamino)-3-(3,4-dichlorobenzylideneamino)guanidine used therein other active compounds, there are obtained similar results indicating the anti- *G. lamblia* activities of the compounds included above in Table 1.

Similarly, following essentially the same procedure described above, the hydrochloride salts of compounds (2) to (10) included in Table 1 are found to be as equally active as the corresponding free bases.

EXAMPLE 2

Employing essentially the same method of Example 1, centrifuged cells of *T. vaginalis* 30001 are inoculated with 1-(4-chlorocinnamylideneamino)-3-(3,4-dichlorobenzylideneamino)guanidine at 37° C. for 24 hours. The results indicate that this compound is also an effective anti- *T. vaginalis* agent with an $ED_{50}$ value of 2.25.

Similarly, previously described compounds (2) to (10) and the pharmaceutically acceptable salts thereof an active anti- *T. vaginalis* agents as shown in Table 1.

EXAMPLE 3

| Preparation of Capsule Formulation | |
|---|---|
| Ingredient | Milligrams per Capsule |
| 1-(4-cyanocinnamylideneamino)-3-(4-chlorobenzylideneamino)-3-methyl-guanidine | 10 |
| Starch | 100 |
| Magnesium Stearate | 10 |

The active ingredient, starch and magnesium stearate are blended together. The mixture is used to fill hard shell gelatine capsules of a suitable size at a fill weight of 120 mg per capsule.

EXAMPLE 4

| Preparation of Tablet Formulation | |
|---|---|
| Ingredient | Milligrams per Tablet |
| 1-(3,4-dichlorocinnamylideneamino)-3-(4-trifluoromethylbenzylideneamino)-3-methyl-guanidine | 12 |
| Lactose | 200 |
| Corn starch (for mix) | 50 |
| Magnesium stearate | 6 |

The active ingredient, lactose and corn starch (for mix) are blended together. The corn starch (for paste) is suspended in water at a ratio of 10 grams of corn starch per 80 milliliters of water and heated with stirring to form a paste. This paste is then used to granulate the mixed powders. The wet granules are passed through a No. 8 screen and dried at 120° F. The dry granules are passed through a No. 16 screen. The mixture is lubricated with magnesium stearate and compressed into tablets in a suitable tableting machine. Each tablet contains 12 milligrams of the active ingredient.

What is claimed is:

1. A method for treating giardiasis and trichomoniasis in humans which comprises the administration to a person in need of such therapy an amount effective for the treatment of giardiasis and trichomoniasis of a 1-(cinnamylideneamino)-3-benzylideneaminoguanidine of the formula:

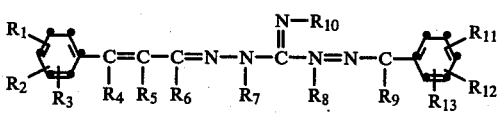

and a pharmaceutically acceptable acid addition salt thereof wherein:

(a) $R_1$ and $R_{11}$ are each hydrogen, halo, nitro, trifluoromethyl, trifluoromethoxy, trifluoromethylthio, acetyl, carbamoyl, cyano, methylsulfinyl, methylsulfonyl, carbomethoxy or dimethylaminosulfonyl;

(b) $R_2$ and $R_{12}$ are each hydrogen, halo or nitro;

(c) $R_3$ and $R_{13}$ are each hydrogen or halo, at least one of $R_1$, $R_2$, $R_3$, $R_{11}$, $R_{12}$ and $R_{13}$ is a substituent other than hydrogen;

(d) $R_4$ and $R_5$ are each hydrogen, halogen or lower alkyl;

(e) $R_6$, $R_7$, $R_8$ and $R_9$ are each hydrogen or lower alkyl; and (f) $R_{10}$ is hydrogen, lower alkyl or lower alkanoyl.

2. The method of claim 1 wherein the 1-(cinnamylideneamino)-3-benzylideneaminoguanidine is selected from the group consisting of (a) 1-(4-chlorocinnamylideneamino)-3-(3,4-dichlorobenzylideneamino)guanidine;

(b) 1-(4-trifluoromethylcinnamylideneamino)-3-(4-chlorobenzylidenamino)-3-methyl-guanidine;

(c) 1-(4-cyanocinnamydieneamino)-3-(4-chlorobenzylideneamino)-3-methyl-guanidine;

(d) 1-(3,4-dichlorocinnamylideneamino)-3-(4-chlorobenzylideneamino)-3-methylguanidine;

(e) 1-(4-cyanocinnamylideneamino)-3-(4-trifluoromethylbenzylideneamino)-3-methylguanidine;
(f) 1-(3,4-dichlorocinnamylideneamino)-3-(4-trifluoromethylbenzylideneamino)-3-methyl-guanidine;
(g) 1-(3,4-dichlorocinnamylideneamino)-3-(4-cyanobenzylideneamino)guanidine;
(h) 1-(4-chlorocinnamylideneamino)-3-(4-chlorobenzylideneamino)-3-methyl-guanidine;
(i) 1-(4-chlorocinnamylideneamino)-3-(4-trifluoromethylbenzylideneamino)-3-methylguanidine; and
(j) 1-(4-trifluoromethylcinnamylideneamino)-3-(4-nitrobenzylideneamino)-3-methyl-guanidine.

* * * * *